(12) United States Patent
Fregoso et al.

(10) Patent No.: US 11,129,698 B2
(45) Date of Patent: Sep. 28, 2021

(54) ELECTRICAL DISCHARGE IRRIGATOR APPARATUS AND METHOD

(71) Applicant: AMERICAN EAGLE INSTRUMENTS, INC., Missoula, MT (US)

(72) Inventors: Gilbert Fregoso, Fallbrook, CA (US); Brad Heckerman, Lakeside, MT (US); Yuval Charles Avniel, Missoula, MT (US); Dennis Meuchel, Missoula, MT (US)

(73) Assignee: G&H Technologies, LLC, Kalispell, MT (US)

(*) Notice: Subject to any disclaimer, the term of this patent is extended or adjusted under 35 U.S.C. 154(b) by 124 days.

(21) Appl. No.: 15/022,353

(22) PCT Filed: Feb. 28, 2014

(86) PCT No.: PCT/US2014/019474
§ 371 (c)(1),
(2) Date: Mar. 16, 2016

(87) PCT Pub. No.: WO2015/041713
PCT Pub. Date: Mar. 26, 2015

(65) Prior Publication Data
US 2016/0228690 A1    Aug. 11, 2016

Related U.S. Application Data

(63) Continuation of application No. PCT/US2013/060943, filed on Sep. 20, 2013.

(51) Int. Cl.
*A61C 17/20* (2006.01)
*A61N 1/32* (2006.01)
(Continued)

(52) U.S. Cl.
CPC ............ *A61C 17/20* (2013.01); *A61B 18/042* (2013.01); *A61C 1/06* (2013.01); *A61C 1/07* (2013.01);
(Continued)

(58) Field of Classification Search
CPC ...... A61N 1/04; A61N 1/0448; A61N 1/0428; A61N 1/0408; A61N 1/0548; A61N 1/306;
(Continued)

(56) References Cited

U.S. PATENT DOCUMENTS 5,254,121 A    10/1993  Manevitz et al.
5,636,100 A *   6/1997  Zheng ..................... H01G 4/20
                                                   361/311

(Continued)

FOREIGN PATENT DOCUMENTS

DE    102004040045 B3    2/2006
WO         1994016809    8/1994
(Continued)

OTHER PUBLICATIONS

Supplementary European Search Report issued by the EPO for European Patent Application No. 14846176.7 dated Jun. 1, 2017.
(Continued)

*Primary Examiner* — Nicholas D Lucchesi
*Assistant Examiner* — Hao D Mai
(74) *Attorney, Agent, or Firm* — Heslin Rothenberg Farley & Mesiti P.C.

(57) ABSTRACT

An electrical discharge irrigation device and method is described. An electrical discharge irrigation device includes a power source, a circuit coupled to the power source, and an output tip coupled to the circuit. The output tip includes a first end and a second end and a longitudinal axis extending between them, an electrode located in an interior space
(Continued)

of the output tip configured to receive an electrical charge from the circuit and to release an electric discharge, and a ground return including an inner surface of the output tip, wherein a space between the electrode and the ground return comprises a conductive medium, the conductive medium being in contact with the electrode and the ground return to produce the electric discharge.

17 Claims, 9 Drawing Sheets

(51) Int. Cl.

| | |
|---|---|
| *A61B 18/04* | (2006.01) |
| *A61C 5/40* | (2017.01) |
| *A61C 1/06* | (2006.01) |
| *A61C 3/00* | (2006.01) |
| *A61C 17/02* | (2006.01) |
| *A61C 19/06* | (2006.01) |
| *A61C 1/07* | (2006.01) |
| *A61L 2/025* | (2006.01) |
| *A61L 2/10* | (2006.01) |
| *A61L 2/14* | (2006.01) |
| *A61L 2/18* | (2006.01) |
| *A61N 1/05* | (2006.01) |
| *A61N 5/06* | (2006.01) |
| *A61C 17/16* | (2006.01) |
| *A61N 1/04* | (2006.01) |
| *A61N 1/44* | (2006.01) |
| *A61N 1/30* | (2006.01) |
| *A61C 5/50* | (2017.01) |
| *A61L 2/00* | (2006.01) |
| *A61L 2/22* | (2006.01) |

(52) U.S. Cl.
CPC ............... *A61C 3/00* (2013.01); *A61C 5/40* (2017.02); *A61C 5/50* (2017.02); *A61C 17/0202* (2013.01); *A61C 17/16* (2013.01); *A61C 19/063* (2013.01); *A61L 2/025* (2013.01); *A61L 2/10* (2013.01); *A61L 2/14* (2013.01); *A61L 2/18* (2013.01); *A61N 1/04* (2013.01); *A61N 1/0448* (2013.01); *A61N 1/0548* (2013.01); *A61N 1/306* (2013.01); *A61N 1/325* (2013.01); *A61N 1/44* (2013.01); *A61N 5/0603* (2013.01); *A61B 2217/007* (2013.01); *A61L 2/00* (2013.01); *A61L 2/0088* (2013.01); *A61L 2/22* (2013.01); *A61L 2202/25* (2013.01); *A61N 2005/0606* (2013.01); *A61N 2005/0661* (2013.01); *F04C 2270/0421* (2013.01)

(58) Field of Classification Search
CPC ........ A61N 1/325; A61N 1/44; A61N 5/0603; A61N 2005/0606; A61B 18/14; A61C 5/40; A61C 5/50; A61C 1/06; A61C 17/0202; A61C 19/063
USPC ............... 433/32; 606/32–52, 169; 604/114; 422/186.04
See application file for complete search history.

(56) References Cited

U.S. PATENT DOCUMENTS

| | | | |
|---|---|---|---|
| 6,749,604 B1* | 6/2004 | Eggers | A61B 18/12 604/114 |
| 7,678,069 B1* | 3/2010 | Baker | A61B 18/12 604/22 |
| 8,137,341 B2 | 3/2012 | Fugo | |
| 8,956,352 B2* | 2/2015 | Mauch | A61B 18/1492 606/41 |
| 9,924,992 B2* | 3/2018 | Hoey | A61B 18/082 |
| 2002/0111608 A1 | 8/2002 | Baerveldt et al. | |
| 2005/0070894 A1* | 3/2005 | McClurken | A61B 18/1492 606/48 |
| 2007/0208334 A1 | 9/2007 | Woloszko et al. | |
| 2007/0208335 A1* | 9/2007 | Woloszko | A61B 18/148 606/41 |
| 2008/0039834 A1* | 2/2008 | MacKay | A61B 18/042 606/46 |
| 2008/0097425 A1 | 4/2008 | Truckai | |
| 2008/0138761 A1* | 6/2008 | Pond | A61C 5/40 433/29 |
| 2008/0208189 A1* | 8/2008 | Van Wyk | A61B 18/04 606/42 |
| 2009/0143718 A1 | 6/2009 | Jiang et al. | |
| 2009/0270849 A1* | 10/2009 | Truckai | A61B 18/042 606/13 |
| 2010/0209867 A1* | 8/2010 | Becker | A61C 5/02 433/32 |
| 2011/0270242 A1* | 11/2011 | Marion | A61B 18/148 606/35 |
| 2011/0276113 A1* | 11/2011 | Cybulski | A61B 18/042 607/101 |
| 2011/0282340 A1* | 11/2011 | Toth | A61B 18/042 606/33 |
| 2012/0046598 A1* | 2/2012 | Kardos | A61N 1/0416 604/20 |
| 2012/0237893 A1 | 9/2012 | Bergheim et al. | |
| 2012/0245580 A1* | 9/2012 | Germain | A61B 18/042 606/41 |
| 2012/0276499 A1* | 11/2012 | Devery | A46B 11/0017 433/32 |
| 2013/0030426 A1* | 1/2013 | Gallardo | A61B 18/1492 606/33 |
| 2013/0196286 A1 | 8/2013 | Rutberg et al. | |
| 2015/0238755 A1* | 8/2015 | Fregoso | A61C 3/00 433/29 |
| 2015/0306411 A1* | 10/2015 | Srb | A61B 18/042 604/23 |
| 2018/0036059 A1* | 2/2018 | Ward | A61B 18/042 |

FOREIGN PATENT DOCUMENTS

| | | |
|---|---|---|
| WO | 1998003117 | 1/1998 |
| WO | 1999020213 | 4/1999 |
| WO | 2009128579 A1 | 10/2009 |
| WO | 2010052717 A1 | 5/2010 |
| WO | 2011123124 A1 | 10/2011 |

OTHER PUBLICATIONS

International Search Report for PCT/US2014/019474 dated May 7, 2014.
Extended European Search Report issued by the EPO for European Patent Application No. 13864734.2 Aug. 11, 2016.
Extended European Search Report issued by the EPO for European Patent Application No. 19179168.0 dated Dec. 19, 2019.
Extended European Search Report issued by the EPO for European Patent Application No. 19168413.3 dated Aug. 2, 2019.

* cited by examiner

ELECTRICAL DISCHARGE IRRIGATOR APPARATUS AND METHOD

CROSS-REFERENCE TO RELATED APPLICATION

This application is a continuation-in-part of PCT Application No. PCT/US13/60943, entitled "ELECTRICAL DISCHARGE IRRIGATOR APPARATUS AND METHOD," filed Sep. 20, 2013, which claims the benefit of PCT/US12/70080, entitled "ELECTRICAL DISCHARGE IRRIGATOR APPARATUS AND METHOD," filed Dec. 17, 2012, which claims the benefit of U.S. Provisional Application No. 61/699,568, filed Sep. 11, 2012. This application claims priority to both filed PCT applications, and all listed applications are incorporated herein, by reference, in their entirety. This application is related to commonly owned, co-pending design patent application Ser. No. 29/483,570, entitled "TISSUE BORING DRILL TIP," filed on Feb. 28, 2014, co-pending design patent application Ser. No. 29,483,572, entitled "FOCUSED TISSUE BORING TIP WITH WATER VENT," filed on Feb. 28, 2014, co-pending design patent application Ser. No. 29/483,574, entitled "MULTI-DIRECTIONAL TISSUE REAMER," filed on Feb. 28, 2014, co-pending design patent application Ser. No. 29/483,576, entitled "SINGLE VENT DIRECTIONAL REAMER TIP," filed on Feb. 28, 2014, co-pending design patent application Ser. No. 29/483,581, entitled "IRRIGATION TIP filed on Feb. 28, 2014, co-pending design patent application Ser. No. 29/483,582, entitled "MODIFIED IRRIGATION TIP" filed on Feb. 28, 2014, which are hereby incorporated herein by reference in their entirety.

FIELD OF INVENTION

The present invention relates to an apparatus and method of utilizing acoustic waves created by an electrical discharge for irrigation and disinfection.

BACKGROUND OF INVENTION

Foreign bodies, such as bacteria and microbes pose a risk to dental health. These foreign bodies can invade canals and other hard to reach areas in dental structures and compromise dental health. It is the infections that are caused by the persistence of these foreign bodies that pose one of the greatest risks to the endodontic health of a patient.

Treatments to eliminate harmful canal contents, and therefore reduce the risk of infections, range from invasive treatments, such as extraction, to the far less invasive, yet not always effective, irrigation. Irrigation involves the use of an anti-bacterial solution to flush the canals. Today's irrigation solutions include utilizing direct lift, displacement and/or gravity pumps to move a fluid into canals, utilizing ultrasonic tips at varying rates, utilizing mechanical instruments, such as files, using positive pressure to inject fluid (for example, using a hypodermic needle) and negative pressure to remove it, and combinations of these techniques.

Studies have demonstrated that mechanical instruments alone cannot disinfect root canals. This is because large areas of canal walls, including apical, ribbon-shaped, and oval canals, cannot be cleaned mechanically because mechanical means cannot reach and come into physical contact with all surfaces within the tooth, so microorganisms in these areas can survive. Irrigation solutions are generally required to eradicate these microorganisms and various chemicals have been used for this purpose.

Ideally, an irrigant kills bacteria, dissolves necrotic tissue, lubricates the canal, removes the smear layer, and does not irritate healthy tissue. Presently, solutions that include sodium hypochlorite (NaOCl) and ethylenemide tetra-acetic acid (EDTA) are favored by dentists. The NaOCl solution, usually at a concentration between 1%-3% is used to dissolve tissue and disinfect (remove bacteria), while EDTA removes the smear layer. During an irrigation procedure, NaOCl is used initially to dissolve tissue and disinfect and EDTA is introduced at the end of the procedure to remove the smear layer. The EDTA application is followed by another flush of NaOCl or another inert solution.

Although certainly less invasive than extraction, irrigation has its shortcomings. First, NaOCl, EDTA, and other solutions found effective in irrigation are caustic solutions, including other bleaches, which when applied can badly irritate the mouth and surrounding structures. During an application, there is a risk that these solutions will perforate the apex of the canal, the end of the canal where the nerve meets the bone. If this happens, the results are so painful for a patient that the patient will end up on significant pain management, i.e., prescription pain killers, for at least two days, but sometimes, as long as two months. Second, current irrigation techniques carry a failure rate of up to 5% because often, the procedure fails to remove all the nerve tissue that is infected in the root canal system, so residual bacteria remains. Third, irrigation solutions are only effective at the time that they are applied. After a patient is treated with NaOCl and/or EDTA, the solutions are flushed out and there is no positive residual effect after the treatment is complete. Thus, any bacteria remaining in hard to reach canals will remain indefinitely and can lead to infection.

A need exists for a method and apparatus for effectively irrigating even hard to reach dental canals in a manner that produces residual benefits without causing damage and/or pain in the mouth and surrounding structures.

SUMMARY OF INVENTION

Shortcomings of the prior art are overcome and additional advantages are provided through the provision of an electrical discharge irrigation device that includes a power source, a circuit coupled to the power source; and an output tip coupled to the circuit. The output tip includes a first end and a second end and a longitudinal axis extending between them, an electrode located in an interior space of the output tip configured to receive an electrical charge from the circuit and to release an electric discharge, and a ground return that includes an outside surface of the output tip, where a space between the electrode and the ground return includes a conductive medium, the conductive medium being in contact with the electrode and the ground return to produce the electric discharge.

Shortcomings of the prior art are overcome and additional advantages are provided through the provision of a method of producing at least one of cavitation or plasma discharge the includes obtaining an embodiment of the earlier described electrical discharge irrigation device, which includes a trigger to engage the device, positioning the output tip adjacent to a target, engaging the trigger on the device to control the electric discharge, and utilizing the electrical discharge to create compression waves within the conductive medium inside the output tip, causing the conductive medium in the tip to exit the output tip through the at least one opening in the output tip.

Shortcomings of the prior art are overcome and additional advantages are provided through the provision of an output tip which includes a first end and a second end and a longitudinal axis extending between them, an electrode located in an interior space of the output tip configured to receive an electrical charge from the circuit and to release an electric discharge; and a ground return which includes an outside surface of the output tip, wherein a space between the electrode and the ground return comprises a first conductive medium, the first conductive medium being in contact with the electrode and the ground return to produce an environment for the electric discharge; and at least one aperture extending through the outside surface of the output tip, where the outside surface of the output tip is cylindrical.

In a further aspect of an embodiment of the present invention, the output tip includes at least one opening on the outside surface of the output tip, and the electrical discharge creates cavitation within the conductive medium.

In a further aspect of an embodiment of the present invention, sonoluminescence may occur in response to the cavitation and light is visible to an operator of the device during operation of the device.

In a further aspect of an embodiment of the present invention, a conductive medium exits the output tip through the at least one opening in the tip.

In a further aspect of an embodiment of the present invention, the output tip can be utilized to create an incision in tissue when at least one of the output tip or the conductive medium is positioned adjacent to the tissue.

In a further aspect of an embodiment of the present invention, the output tip further includes a pressure control mechanism.

In a further aspect of an embodiment of the present invention, the output tip includes a malleable material.

In a further aspect of an embodiment of the present invention, the output tip also includes an inner surface and where the electrode opposes the inner surface at a distance. The electrode is cylindrical, the inner surface is cylindrical, and the distance is equal between the electrode and the inner surface when measured from the electrode to the inner surface around the circumference of the electrode.

In a further aspect of an embodiment of the present invention, the output tip also includes an insulating layer in contact with one of the electrode and the ground return, the insulating layer includes at least one perforation, the at least one perforation defining an area for electrical coupling between the electrode and the ground return.

In a further aspect of an embodiment of the present invention, the method includes positioning the output tip adjacent to an object, and making an incision in the object.

In a further aspect of the present invention, the output tip also includes an insulating layer adjacent to the outside surface of the tip; and an insulating layer between the inner surface and the electrode. In this embodiment, the electrode comprises an array of individual electrodes and this tip is adapted for making the aforementioned incisions.

Additional features are realized through the devices and techniques of the present invention. Other embodiments and aspects of the invention are described in detail herein and are considered a part of the claimed invention.

BRIEF DESCRIPTION OF DRAWINGS

The foregoing and objects, features, and advantages of one or more aspects of the invention are apparent from the following detailed description taken in conjunction with the accompanying drawings in which.

DETAILED DESCRIPTION OF THE INVENTION

The apparatus and method of the present invention utilize an electric discharge and creates oscillating pressure to eradicate unwanted matter from a medium. Embodiments of the present invention are used as irrigation systems in endodontic procedures as well as in periodontal procedures, including treatments for periodontal disease and peri-implantitis. These dental irrigation systems include, but are not limited to, an irrigation system for Piezoelectric/Magnetostrictive scalars, irrigation system for cleaning the teeth pockets (e.g., root canals or periodontal or endodontic regions), and removing biofilm, a water pick irrigation system for cleaning the teeth, an irrigation system for flushing the periodontal pocket, and/or an irrigation system for surgery for disinfecting wounds. While some embodiments of the present invention pulse liquid that is external to the device directly, for example, in dental canals in endodontic uses, some embodiments of the present invention contain one or more internal reservoir(s) where the liquid and/or water used is pre-treated (pre-pulsed) before it is released into the treatment area, for example, in Piezoelectric/Magnetostrictive scalars and/or water picks.

An embodiment of the present invention utilized for endodontic procedures comprises a tube with electrodes to deliver an electrical discharge which creates the desired acoustical waves, cavitation related byproducts, and/or plasma, in many of these procedures, the embodiment utilized emit electrical pulses through a tip of an embodiment of the apparatus as spark discharges.

Throughout this application, the terms "tip" and "output tip" are used interchangeably to describe and aspect of embodiments of the present invention.

The electrical pulses agitate the liquid into which the tip is immersed and create acoustic waves, shock waves, cavitation, plasma, sonoluminsence, microjets and additional discharges that kill foreign agents, including toxins, bacteria, and microbes, dissolve necrotic tissue, lubricate the canal, and remove the smear layer while providing antibacterial and anti-microbial benefits both during and after treatment. Thus, an embodiment of the present invention can be utilized to irradiate bacteria and other infectious agents while providing cleaning and irrigation of the tooth canals for proper Root Canal Procedures in accordance with ADA guidelines.

An embodiment of the apparatus is used as a Piezoelectric/Magnetostrictive scalar. As discussed later in greater detail, an embodiment of the present invention utilized for as a Piezoelectric/Magnetostrictive scalar utilizes an ultrasonic tip that disrupts biofilm (bacteria colonies) by using ultrasonic energy to remove the biofilm, and disrupt the bacteria. In an embodiment of this invention, the ultrasonic pulse is provided in a target area at a rate of about 1-99 Hz-with a pulse duration of 100-500 microseconds at power settings ranging from milli-joules to micro-joules to mechanically remove the biofilm, and disrupt the bacteria. Tips utilized in this application comprise an exterior and/or interior water line system that delivers water to cool the tips, provide a medium for the electrical discharge and to flush the periodontic pocket with water. The flushing action cleanses the area of the bacteria that the mechanical action of the tip has disrupted in and/or fractured off the tooth structure.

An advantage of the present invention over ultrasonic based techniques is that embodiments of the present invention do not vibrate, while ultrasonic technologies do vibrate. A vibrating tip, such as that incorporated into ultrasonic devices, causes damage to the structural integrity of a tooth and a reduction in the original tooth structure. In fact, vibration itself can also cause cracks etc. in dental structures. One benefit of embodiments of the present invention is that because they do not vibrate, they do not cause the types of changes to the original tooth structure, including damage, that are associated with ultrasonic based technologies.

By utilizing cavitation to create sonoluminsence, embodiments of the present invention create a light discharge from the tip, which provides an operator of the device with a light guide that indicates that the device is in operation and can assist the operator in targeting the discharge at biological structures that are being targeted by the device and the output tip.

In an aspect of a Piezoelectric/Magnetostrictive embodiment, the water and/or fluid that is pulsed is essentially pre-treated in one or more "holding chambers" internal to the apparatus before it passes into the water lines feeding the tips. Then, as the tip is, used it is this treated water that flushes the pockets and provides better pathogen kill, and long term protection in contrast to current methods of just using water, or a mild chemical agent and water. The current industry-standard treatment, as opposed to embodiment of the present method, has an anti microbial effect, but only while it is actually flushing the pocket. This effect does not continue. In an aspect of a Piezoelectric/Magnetostrictive embodiment, this anti microbial effect will continue after flushing the pocket. Liquids utilized in this application include, but are not limited to, a 2% glutaraldehyde solution. In embodiments of the present invention, liquids used in this application may or may not be generally known anti-microbial solutions like gluteraldehyde, hydrogen peroxide, etc. Pre-treating the water/liquid in internal reservoirs is also utilized in embodiments used to clean periodontic wound sites.

Returning to endodontic uses, an embodiment of the present invention is a hand held irrigation device that generates an electrical discharge, creating acoustical shock waves in an irrigant and UV radiation that irrigate dental canals and other structures during an irrigation treatment, and also introduce one or more of the following: UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions, which act to combat foreign agents after use of the device has ceased. Further embodiments of the present invention are mounted or table top models, as opposed to hand held.

An embodiment of the hand-held version of the present apparatus, which is utilized, for example, for endodontic treatments, is comprised of a handle, which is used to grip and manipulate the apparatus, a body, where various electrical components are housed, and a tip, which contains one or more electrodes and a ground return, which is inserted into a conductive liquid in the mouth of a patient in order to irrigate a selected area using acoustic waves generated by one or more circuits in the apparatus. An embodiment of the tip of the apparatus is comprised of flexible material such that it can be positioned deep within dental canals.

An embodiment of the apparatus contains a low voltage power source and the internal circuitry of the apparatus, discussed later in greater detail, converts the initial low voltage power, to high voltage power, which pulses the liquid into which the tip is immersed. The tip of an embodiment of the present method and apparatus utilizes electrodes comprised of biologically inert materials, including but not limited to, silver, copper, stainless steel, and/or iron (ferrite) which have a toxicity to bacteria and act as an anti-pathogen. Electrodes in further embodiments of the present invention may include ceramic-based electrode, carbon-based electrodes, and other conductive materials. The nanoparticles created by the electrodes, and/or working surface, combat the bacteria and other foreign particles in the canals.

In an embodiment of the present invention, because the electrical discharge itself destroys foreign agents both during and after an irrigation treatment, the irrigant utilized needn't possess antiseptic or anti-bacterial qualities on its own. For example, although NaOCl and EDTA can be used in conjunction with this method, saline and water solutions are also effectively used with this method. In general, any anti-bacterial and/or anti-microbial fluids utilized in irrigation protocols are compatible with this apparatus and method as dielectric liquids transmit the electrical discharge and they may improve its effectiveness in use. Thus, because water is conductive, it works well with the present method and apparatus.

The utilization of the electrical discharge from one or more electrodes in the tip of an embodiment of the present apparatus create(s) "shock waves" in the irrigation fluid which have a high gradient at their front, so the difference in pressure created in the irrigation fluid damages bacterial membranes and/or destroys them. The waves are effective in a given radius and therefore penetrate canals and dental structures that are difficult to reach and thus effectively irrigating them.

The electrical discharges produce the pulsed shock waves, which damage pollutants on a cellular level. The pulses may mechanically destroy bacteria and microbial cells, chemically and permanently change the cells so they cease regular biochemical activity, and/or irreversibly change the genetic system of the cells. Cellular damage sustained by the pollutants includes, but is not limited to, cracking the cell walls without releasing the contents of the cells, and dispersing the cell wall and contents of the cells, DNA disruption.

The embodiment of the tip additionally discharges UV radiation, which when absorbed in different degrees by water molecules, hydrogen peroxide, the other mediums discussed, and/or in the irrigating fluid, produces ozone, $H_2O_2$ and OH radicals, which destroy microbes and also some organic compounds. The electrical discharge of an embodiment of the invention additionally disseminates hydrated electrons, nanoparticles, and positive and/or negative ions (from metal electrodes utilized in various embodiments) which continue anti-microbial and anti-bacterial action against foreign agents after the irrigation procedure has terminated. Embodiments of tips may discharge one or more of the following: UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions.

One advantage of embodiments of the present invention is that they are effective against pollutants yet are able to utilize relatively low power settings over relatively short periods of time and achieve high levels of efficiency. Embodiments of the present invention that use particularly low power settings enable the miniaturization and the simplification of the driving circuit and power requirements. For example, an embodiment of the present invention eradicates foreign agents from a selected medium in 25 seconds-5 minutes at between 20 Hz, the energy in 26 microjoules-4 joules. Some embodiments of the present invention utilize power requirements at least three magnitudes lower than the previous example, i.e., microjoules in place of joules. These settings are exemplary as dependent upon the use of the apparatus and the embodiment of the apparatus, the power settings and the duration of a treatment will vary.

In an embodiment of the present invention, an output tip can be adapted to cut tissue and/or other biological structures when positioned in proximity to the structure. The applications of this cutting functionality are not limited to dental applications. In addition to their endodontic and periodontal applications, one of skill in the art will recognize that embodiments of the present invention can be adapted for additional specific uses. These uses include, but are not limited to, bladder surgery, sinus surgery, cardiovascular surgery, various cancer surgeries, and prostate surgery. In these surgeries, the ability to utilize embodiments of the device and output tips to cut biological structures is of particular use.

In embodiments of the present invention, sonoluminescence may occur during treatment utilizing embodiments of the present device and techniques, which provides light at the working surface which assists an operator in confirming the actuation of the device as well as providing UV light which is known to further remediate microbial/biologic species. However, in further embodiments of the present invention, cavitation can occur without sonoluminescence.

In addition to its aforementioned surgical uses, embodiments of the present invention can also be utilized to assist in sterilization of environments and parts of the body upon which a treatment is being performed. Embodiments of the present invention can be integrated into humidifiers, as well as into neti pots, to name just a few integrations.

Embodiments of the present invention can also be utilized in the remediation of biotica species. For example, microorganisms related to fecal matter can be remediated in a targeted area by applying the discharge from the present invention. Use of embodiments the present invention to remediate microorganisms is not limited to remediating those associated with fecal matter as this is offered only as an example. As a further example, embodiments of the present invention can be effective in remediating tetanus and *E. coli*.

Embodiments of the present invention can also be utilized to activate materials in situ, activating these materials to provide remediation of pollutants, including but not limited to, bacteria and microorganisms.

Aforementioned PCT Application No. PCT/US13/60943 and PCT/US12/70080, which are incorporated herein in their entirety, include descriptions and figures that describe various embodiments of the present invention, including some examples of circuits that can be utilized in embodiments of the present invention to assist in creating the electrical charges, including the cavitation and plasma discharges.

Figure 1:
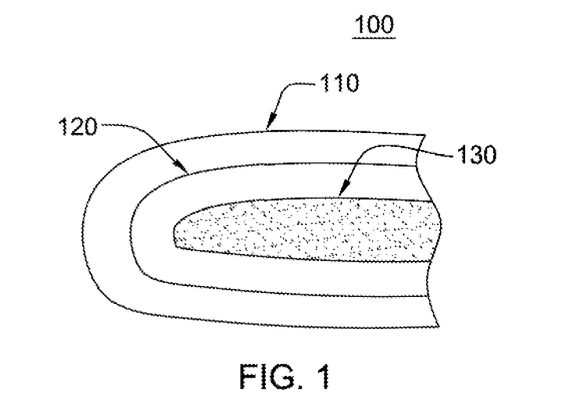
FIG. 1 depicts an aspect of embodiment of the present invention.

In an embodiment of the present invention, output tips can be used to cut targeted areas and the cutting functionality is enabled by the use of embodiments of the output tip specifically adapted for this purpose. Embodiments capable of cutting functionality include a center electrode that is comprised of an array of electrodes. In one embodiment, the outside of the tip is comprised of an insulating material, which is in contact with a ground return. Between the ground return and the center conductor, as it can be referred to in conjunction with this embodiment for ease of understanding, is additional insulation. The center conductor is an array. Thus, when the circuit, which is part of embodiment of the device is loaded, in can deliver to individual electrode in the array. FIG. 1 depicts the structure of an embodiment of a cutting tip utilized in an embodiment of the present invention and FIG. 2 depicts an exemplary configuration for the described array.

Referring to FIG. 1, an embodiment of an output to 100 is depicted. This tip includes insulation of the outer surface 110, adjacent to a ground return 120. An insulating layer 130 is positioned between the ground return 120 and center conductor 130. In an embodiment of the present invention, this insulating layer is perforated to allow electrical coupling between the ground and the center conductor 130.

The center conductor 130 is comprised of more than one electrode oriented in an array. Referring to FIG. 2, the central conductor 130 of FIG. 1, which is an array, can be understood as a cluster array 200 and when a circuit used in the present device and/or technique is loaded, the circuit is capable of delivering to the individual electrodes that comprise the cluster array 200. This cluster array 200 enables the output tip 100 to produce multiple discharges as one time.

Figure 2:
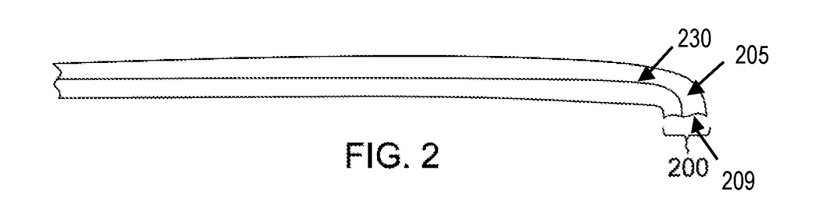
FIG. 2 depicts an aspect of an embodiment of the present invention.

When placed in a conductive solution, the output tip 100 of FIG. 1, with the center electrode array 200 in FIG. 2 will churn this liquid. When voltage is applied to the device comprising this tip from a power source, the output tip enables precise utilization of the multiple discharges, for example, to cut biological material, such as tissue. In this way, and embodiment of the present invention can be utilized to blast anisotropic structures.

Returning to FIG. 2, the individual electrodes in the array can be comprised of a variety of conductive materials, including but not limited to, silver. An advantage of utilizing silver in the electrodes is that because water treated with silver electrodes has the highest bactericidal activity because ions of silver have the highest toxicity to bacteria, it is an anti-pathogen. Thus, the nanoparticles created by the silver electrodes also combat the bacteria and foreign particles. Further embodiments of the present invention utilize electrodes comprised from additional materials that are biologically inert. Materials used to comprise the electrodes include but are not limited to silver, copper, stainless steel, ceramic, carbon-based material, iron, and/or other conductive materials. The suspensions utilized with an embodiment of the present invention can also contain nanoparticles, which further aid in the efficacy of embodiments of the device in combating bacteria and foreign particles. The use of silver electrodes is not confined to the embodiment of FIG. 2, which is used as an illustrative example. This array of electrodes is just offered as an example.

Figure 7:
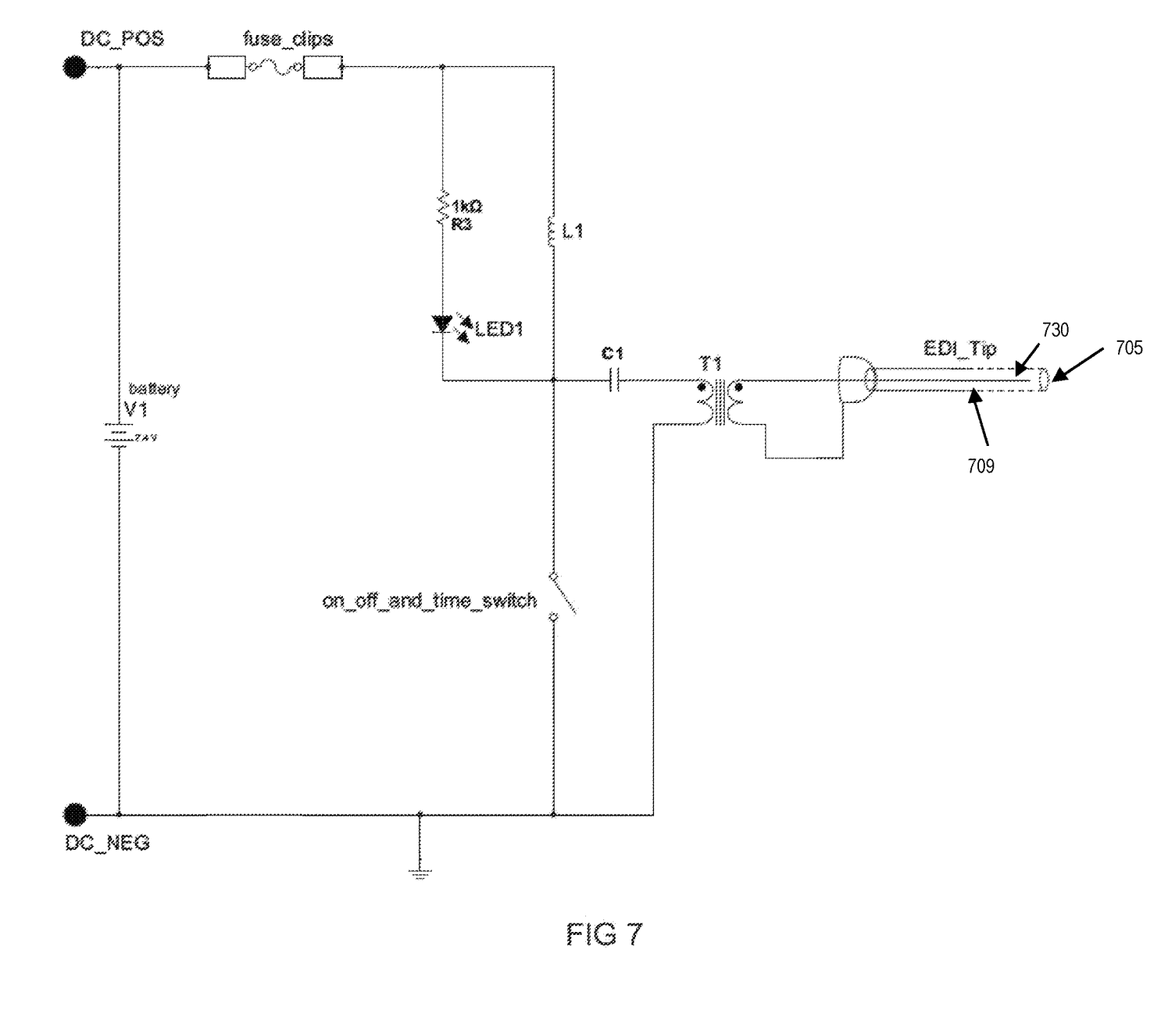
FIG. 7 depicts an aspect of embodiment of the present invention.

Referring to FIG. 2, the electrode 230 is cylindrical, the inner surface 205 is cylindrical, and the distance 209 is equal between the electrode and the inner surface when measured from the electrode 230 to the inner surface 205 around the circumference of the electrode 230. FIG. 7 also illustrates the inner surface 705 being cylindrical and the distance 709 being equal between the electrode 730 and the inner surface 705 when measured from the electrode 730 to the inner surface 705 around the circumference of the electrode 730.

Figure 3:
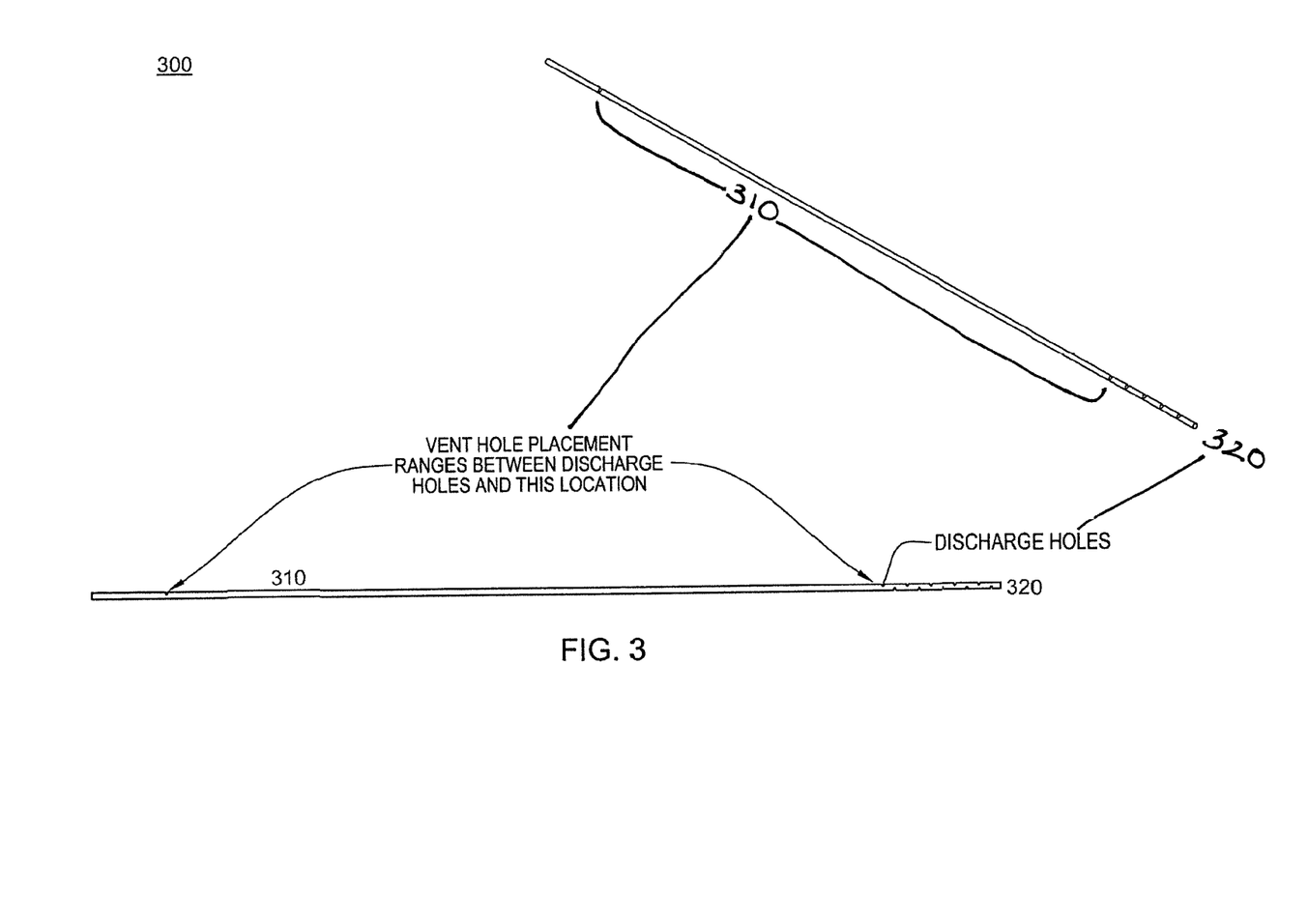
FIG. 3 depicts an aspect of an embodiment of the present invention.

Referring the FIG. 3, an embodiment of the present invention may include an output tip with a pressure control portion 310. The pressure control portion of the output tip 300 is utilized during operation of an embodiment of the device in order to control the pressure within the output tip 300 to avoid blowing out the apex 320 of the tip.

Tips utilized in the present technique are most effective in some embodiments of the present invention when the electrode in the tip is centered relative to the ground, which is included in the outer surface of the tip. This geometry is most easily achieved by providing a cylindrical electrode and a cylindrical ground. The efficacy of the tip increases with the geometry and the tip may degrade at a slower rate.

Figure 4:
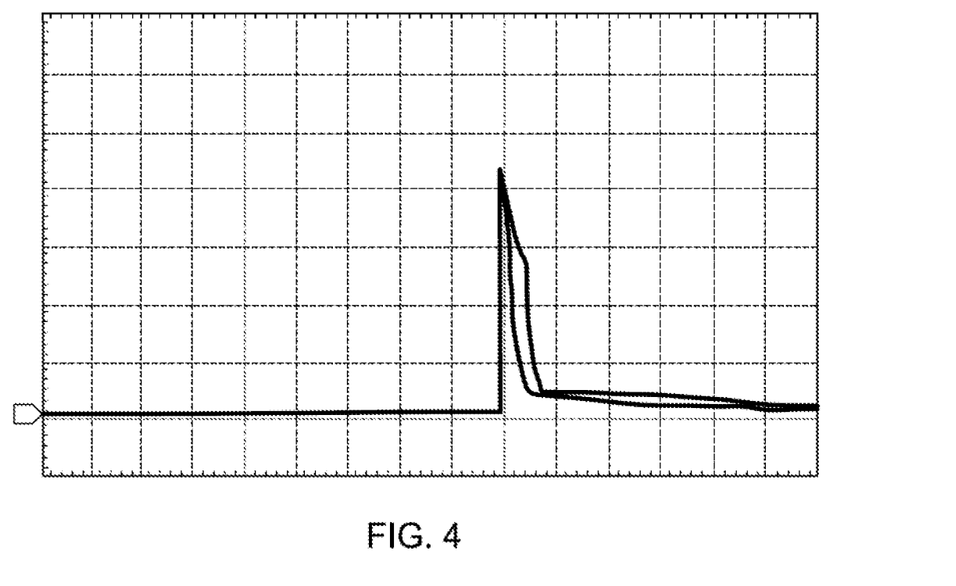
FIG. 4 depicts an oscilloscope trace associated with a degraded electrode utilized in an embodiment of the present invention.
Figure 5:
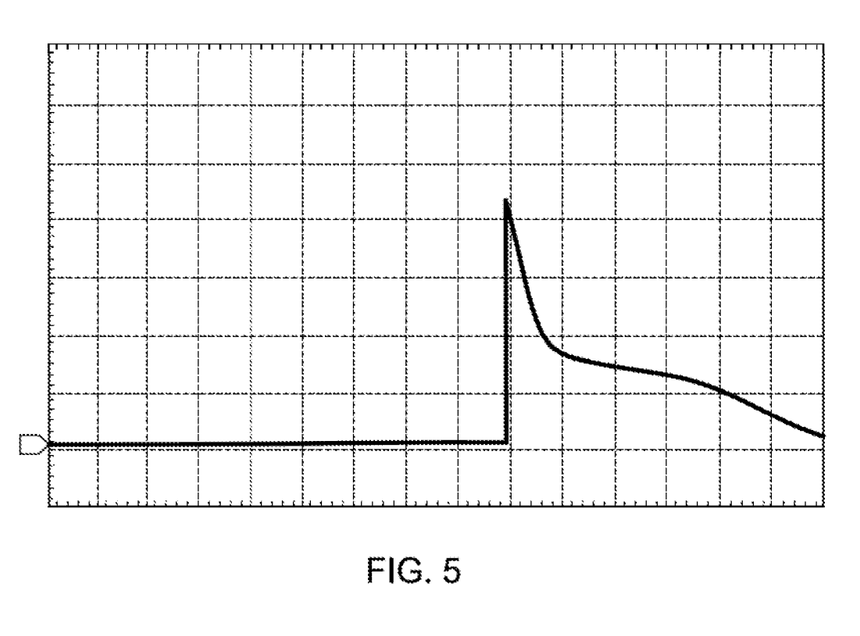
FIG. 5 depicts an oscilloscope trace associated with a degraded electrode utilized in an embodiment of the present invention.

FIGS. 4-5 are captures of oscilloscope graphs associated with tip performance and tip degradation. These graphs record the dielectric behavior of the embodiment of the present system as it changes in reference to ground. The curve can also be described as the discharge curve as a function of time. The "tighter" the curve, the more effective the discharge.

FIG. 4 depicts an embodiment of an output tip starting to show the very first signs of degradation. This figure shows an oscilloscope trace with very little area under the recorded curve. The graph shows a highly vertical trace, i.e., straight up and almost straight down. This graph captured the initial degradation of the tip. The graph shows two discharge rates. The very tight curve depicts the fastest discharge rate, and the second curve (more area under the curve and angled so that it intersects farther down the X-axis) shows slightly slower discharge rate. As the electrode wears, the dielectric behavior degrades, as does the cavitation behavior.

FIG. 5 depicts an oscilloscope trace associated with a degraded electrode. The change in the shape of the curve is noticeable in this figure. The expansion horizontally (expansion into the time domain), relates a degradation of dielectric behavior in the system, which also means a degradation of the discharge characteristics (longer time to discharge). These degradations in turn result in decreased cavitation.

Embodiments of the present invention include features that an operator can utilize to observe whether the tip attached to the device is degrading. The characteristics used to define the usable life of a tip are electrical characteristics and are therefore measurable and recordable. This measurement (or feedback) can be integrated into embodiments of the present invention that include a display, such as an LCD display to both stop the operation of the system upon degradation and apprise the operator to change the tip.

Embodiments of the present invention can be utilized with established protocols in the dental applications previously discussed. However, the unique advantages of the device allow it to be operated with newly established protocols as well. The method that follows is a proposed standard operating procedure (SOP) for the use of an embodiment of the present invention in a root canal procedure. This SOP is offered as an example and one of skill in the art will recognize that variations of this SOP can be performed utilizing embodiments of the present invention and achieve the advantages through the use of embodiments of the present invention. This SOP is depicted by the workflow in FIG. 6.

Figure 6:
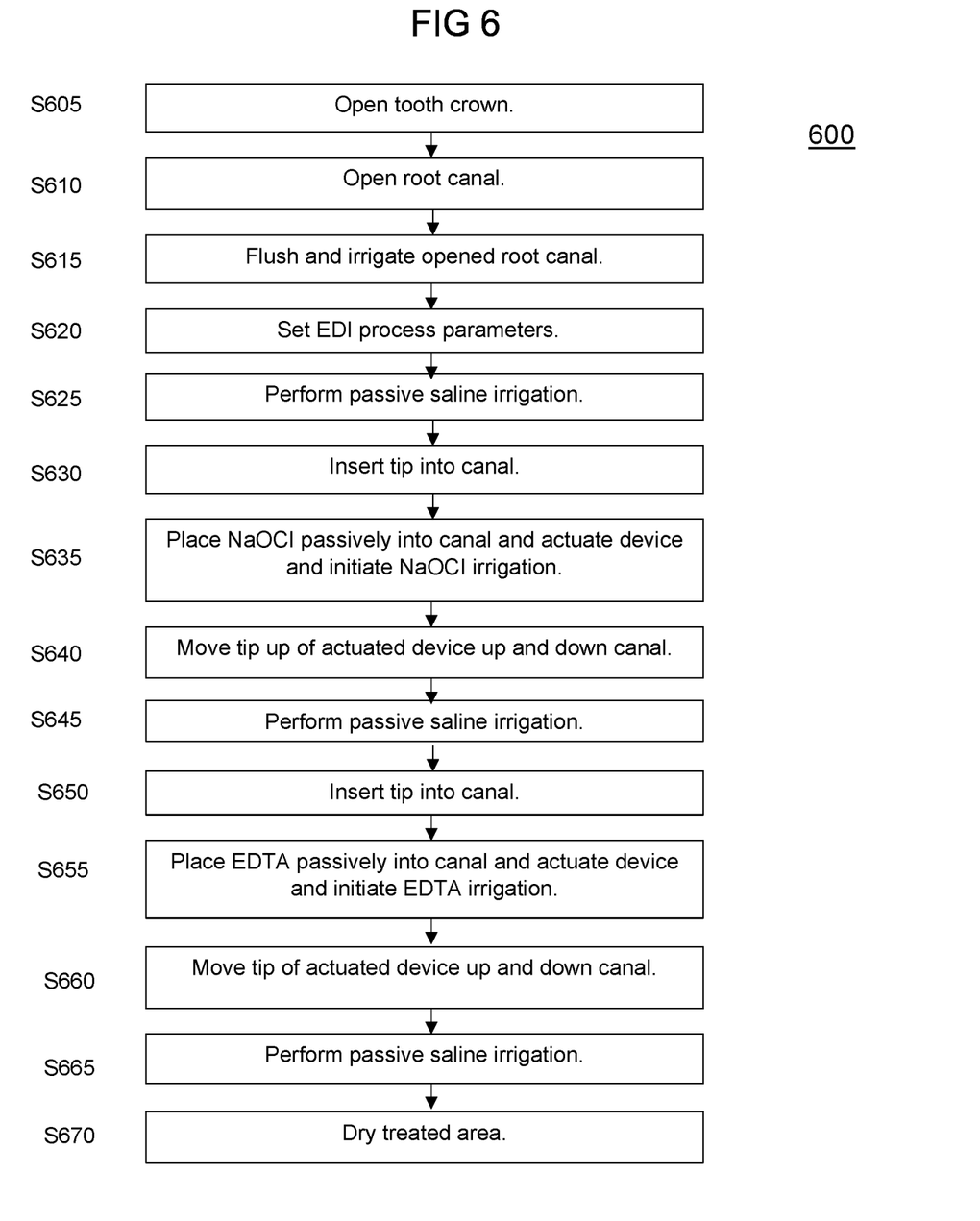
FIG. 6 depicts an exemplary method performed utilizing an embodiment of the present invention.

In this method, before utilizing the present invention, the tooth crown and the root canal are opened. To open the tooth crown (S605), first, a dental drill to open crown of tooth to gain access to pulp and top of canal. Then, the crown opening is rinsed with a solution, for example, a saline solution (e.g. 5 mL). To open the root canal (S610), the following series of endodontic files are used to open the root canal and to remove the majority of necrotic tissue and pulp within the root canal (e.g., red pulp in the case of true teeth): #15 endo file, #20 endo file, #30 endo file. In the case that the #30 endo file is sticky or does not enter, the #25 endo file can be used after the #20 file and prior to the #30 file.

When utilized in this SOP, files should be rotated (or spun) back and forth between the thumb and a finger to gain access towards the apex of the canal. It is recommended that an individual performing the SOP use a rotation and an ingress/egress motion, to both open the canal and remove necrotic tissue and pulp within said canal. It is important to remove pulp/necrotic tissue from the opening in the crown during this process and particular between different files, thereby insuring that the removed tissue is not re-introduced during the filing process. Files should not be forced into the canal, rather an individual performing the protocol should use the cutting ability of the file in conjunction with rotation and ingress/egress motion to gain access and remove tissue.

After opening the canals with the files, an individual can flush and irrigate opened root canal (e.g., with 5 mL of saline solution) to remove any loose debris from the root canal and/or opened crown (S615). Multiple root canals may require individual irrigation cycles.

Now that the canals are open, an embodiment of the EDI device can be utilized to in this process. Please note that embodiments of the described EDI device can also replace files, but the purpose of this SOP is to show how the EDI processing accomplished by an embodiment of the present invention can be integrated into a familiar protocol. Approved protocols include the use of saline, NaOCl, and EDTA. Thus, this protocol employs these solutions as well.

Process parameters are set on an embodiment of the device (S620). These parameters include: process time, frequency, and power setting. Additionally, an output tip is selected for use. These parameters and the tip selection can change depending upon the operator's evaluation of the procedure and what is needed for a successful outcome.

After establishing the process parameters for the EDI processing, the individual performing the root canal places a saline irrigation syringe passively into the canal (S625), as far as possible up the root canal without binding and irrigate with 5 mL of saline solution. This operator then inserts the output tip passively into root canal (S630) as far down in the canal as possible, without binding within the canal. The operator then places a syringe containing 5 mL of 6% NaOCl passively into canal and at the same time, the operator actuates the embodiment of the present device and initiates NaOCl irrigation (S635).

While the device is actuated, the operator moves the EDI tip up and down the canal being treated such that the entirety of the canal "sees" actuation from the EDI tip (S640). In one example, irrigation, using 5 mL of NaOCl, and EDI actuation should last for the total time of treatment (60 seconds). That is, use a steady flow of irrigant for the total EDI treatment time.

After using the NaOCl, the operator then places saline irrigation syringe passively into the canal (S645), as far as possible up the root canal without binding and irrigate with 5 mL of saline solution. Then, the operator can insert the output tip passively into root canal (S650) as far down said canal as possible without binding within the canal. The operator then places a syringe containing 5 mL of 17% EDTA solution passively into canal and at the same time, actuate the device and initiate EDTA irrigation (S655). The operator then moves the tip up and down the canal being treated (S660) such that the entirety of the canal "sees" actuation from the tip. In this protocol, irrigation, using 5 mL of EDTA, and EDI actuation should last for the total time of treatment (60 seconds). That is, use a steady flow of irrigant for the total EDI treatment time.

After the EDTA treatment, the user again places saline irrigation syringe passively into the canal (S665), as far as possible up the root canal without binding and irrigate with 5 mL of saline solution and dries the area (e.g., with paper points) (S670).

As explained in PCT Application No. PCT/US13/60943 and PCT/US12/70080, a variety of circuits can be integrated into embodiments of the present invention, provided that a useable voltage is supplied to the tip to create the reactions to create the byproducts discussed. However, FIGS. 7-8 are examples of additional circuit designed that can be used with embodiments of the present invention and the specific output tips disclosed herein, in PCT/US13/60943, and in [ADD REFERENCE TO DESIGN APPLICATIONS].

FIG. 7 is an example of a circuit that can be integrated into embodiments of the invention that is compatible with output tips utilized in applications discussed herein including irrigation and cutting. Most notably, this embodiment utilizes a push switch as a timing circuit. In FIG. 7, LED1 is a visual indicator that assists an operator in monitoring the operation of the device. However, further embodiment of this invention may not include this feature. Battery v1 provides a power source for the embodiment utilizing this circuit, and the device is actuated with a switch, the on_off_and-_time_switch. When the switch is closed to complete the circuit, a high voltage pulse travels from the capacitor c1 to the transformer T1 to create a high voltage pulse.

Figure 8:
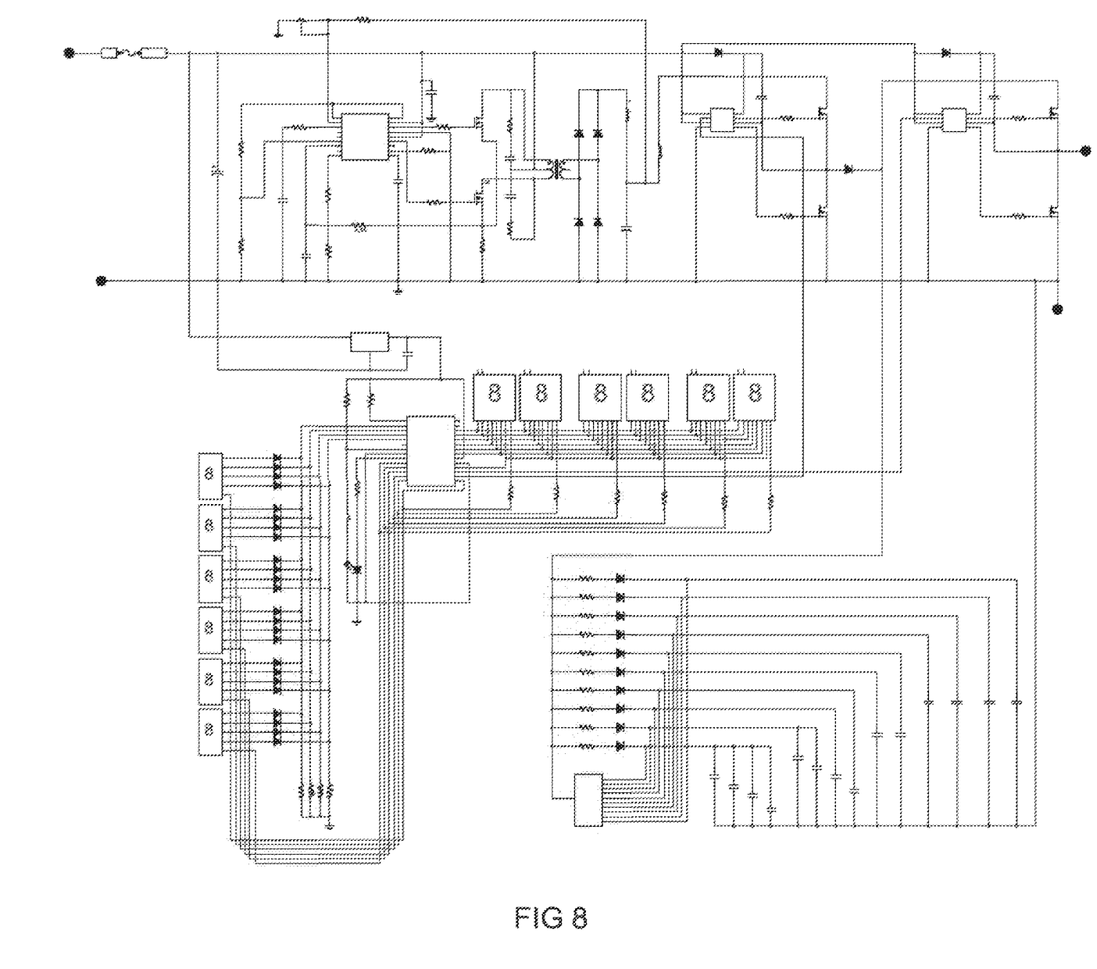
FIG. 8 depicts an aspect of an embodiment of the present invention.

FIG. 8 is an example of another circuit utilized in embodiments of the present invention. Use of this electrical schematic enables the embodiments of the present invention to utilize 10 different power settings. Additionally, embodiments with this component are capable of delivering a precision amount of power to tips, including the smallest tips utilized in connection with this device.

Figure 9:
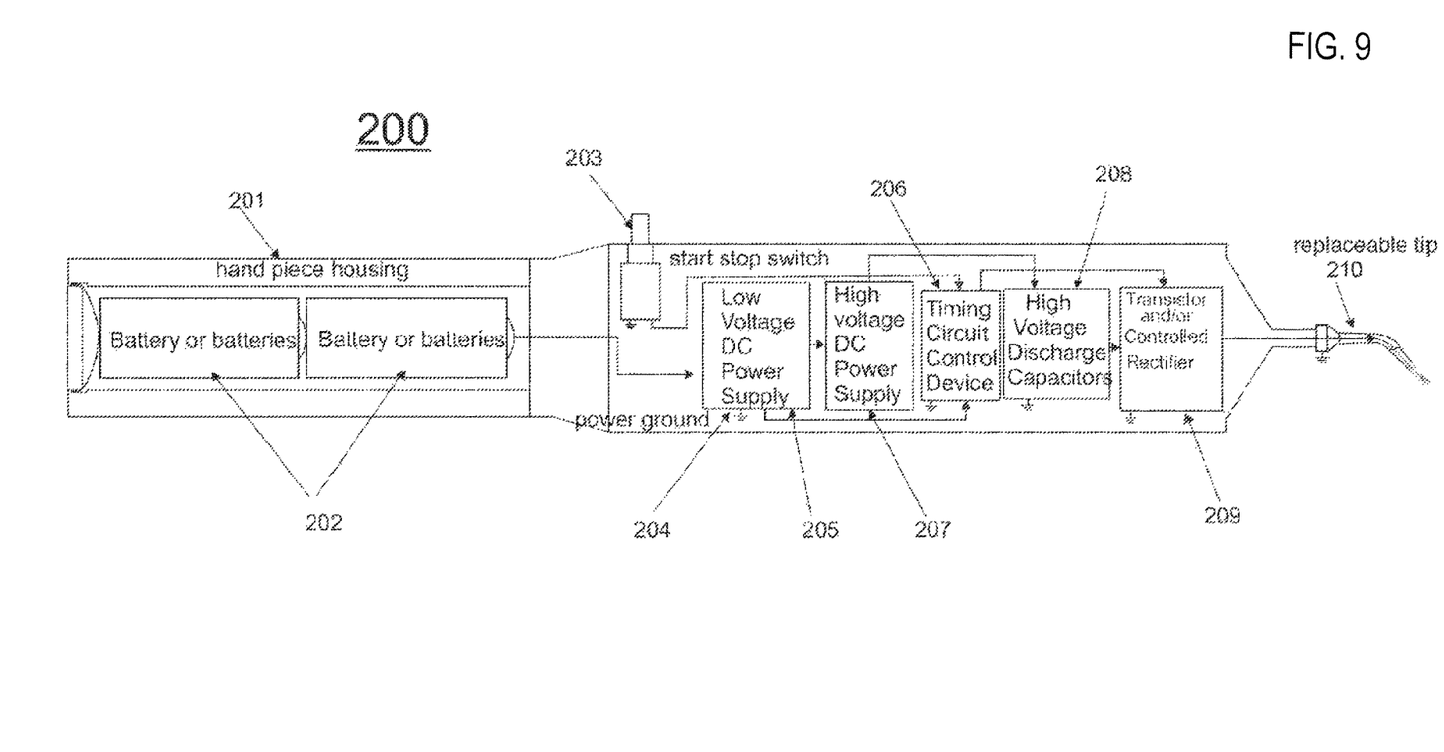
FIG. 9 depicts an aspect of an embodiment of the present invention.

FIG. 9 is another embodiment of the electrical discharge irrigation device apparatus 200. The embodiment of FIG. 9 does not utilize a spark gap or an igniter. FIG. 9 is molded of a non-conductive material, such as plastic, and the hand piece housing 201 is also molded as such that allows for easy cleaning and easy replacement of the batteries 202 within. In another embodiment of the present invention, the housing is conductive and serves as a ground return. Embodiments that utilize plastic, non-conductive housings may reduce manufacturing costs.

Returning to FIG. 9, the two compartments for the batteries 202 in this embodiment are shown as a non-limiting example. Depending upon the batteries selected, the number used to achieve the acoustical pulse (and control the cavitation) generated by the apparatus varies. Batteries 202 utilized in this embodiment include but are not limited to 0.8vdc-30vdc batteries, and/or 180vdc3-7 volt batteries. In various embodiments of the present invention, the batteries are lithium and the voltage range is 3.6v to 7.4v. The low voltage of the batteries 202 is later magnified by additional components in the embodiment, as in the embodiment of FIG. 1A, to drive the acoustical shock wave in the liquid solution that creates the acoustic effect used, for example, in endodontic irrigation.

In the embodiment of FIG. 9, the batteries 202 deliver voltage and current to operate the circuit. Voltage flows from the batteries 202 to the low voltage power supply 204, which regulates the power to all the integrated circuit and timing circuit 206. Voltage travels from the low voltage power supply 204 to the high voltage power supply 207, which converts the voltage from the batteries 202, to a higher voltage. For example, in various embodiments of the present invention, voltages can be converted from all 160 volts DC to as high as 300 volts DC, or higher.

In the embodiment of FIG. 9, the timing circuit 206 is a micro controller device. In embodiments that utilize an LCD display, or any alternate, display, the timing circuit 206 controls this display. In the embodiment of FIG. 9, the timing circuit 206 controls the start stop switch 203, period time, cycle time, pulse width time, and, if utilized in the embodiment, the start stop switch 203 also controls the electronic trim pot that controls the bus voltage.

The high voltage discharge capacitor 208 is connected to a transistor or a controlled rectifier 209, including but not limited to, a high side low side MOSFET(s), and the high voltage discharge capacitor 208 delivers the power in joules. The high transistor or a controlled rectifier (such as a high side low side MOSFET(s) and driver circuit(s)) 209 is/are controlled by the timing circuit 206. For ease of understanding, in FIG. 9, the transistor or a controlled rectifier are depicted in a single element, but in embodiments of the present invention, this element can include, but is not limited to, a high side low side MOSFET(s) and driver circuit(s). In the transistor or a controlled rectifier 209, the timing circuit 206 controls the the transistor or controlled rectifier. In embodiments that utilize a high side low side MOSFET(s) and MOSFET driver(s), the timing circuit 206 controls the driver circuits, which are connected to MOSFET(s). When the timing circuit 206 sends the signals to the devices, high voltage discharge capacitor(s) 208 delivers the energy to the tip assembly. Energy is discharged at the replaceable tip 210, which creates acoustical shock wave in the liquid into which the replaceable tip 210 is at least partially submerged.

One of skill in the art will recognize that in further embodiment of the present invention, additional electrical components may be substituted for one or more high side low side MOSFETs in embodiments where the high side low side MOSFET(s) and driver circuit(s) are used as the and/or combined with one or more high side low side MOSFETs, to deliver power from the high voltage discharge capacitor 208 to the replaceable tip 210. Electrical components included in various embodiments of the invention to carry out this functionality include, but are not limited to, a transistor, a controlled rectifier, insulated-gate bipolar transistors (IGBTs), silicon-controlled rectifiers (SCRs), bipolar transistors (including NPN and PNP), and Darlington transistors.

Figure 10:
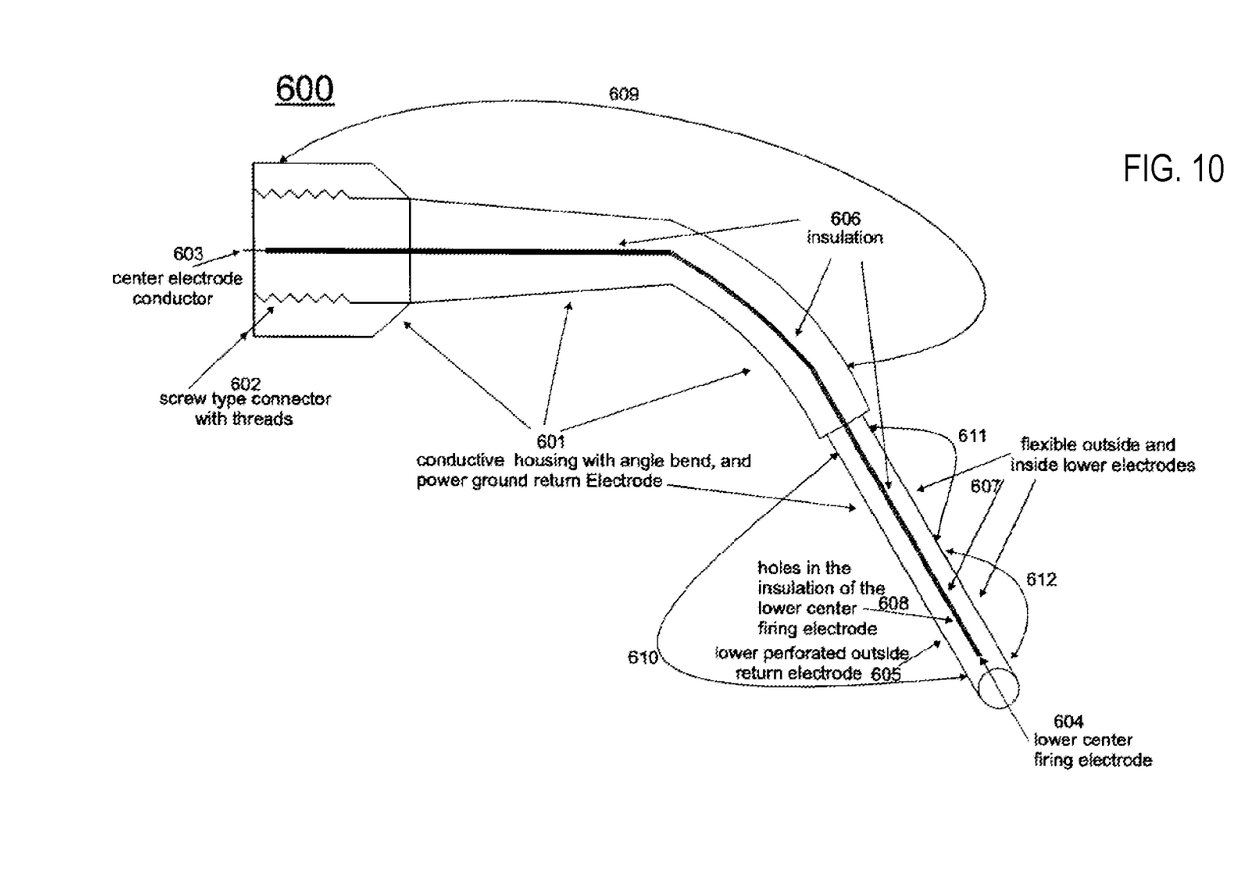
FIG. 10 depicts an aspect of an embodiments of the present invention.

An embodiment of the tip 600 of an embodiment of the apparatus is shown in FIG. 10. The tip 600 appears as an integrated unit, but is separated into components to understand its functionality. During use, the end of the tip 600 is inserted in the mouth of a patient and in some applications, such as cleaning fissures, it may be embedded in a specific tooth that is being irrigated. The tip 600 connects to the body of the apparatus with a connector 602 that is integrated into the tip design. In the embodiment of FIG. 10, the connector 602 is a screw-type connector with threading. The receptors of the threading are located on the body of the apparatus (not pictured).

Like the hand held portion discussed in earlier figures, the tip 600 is comprised of a housing 601. This housing 601 on the tip 600 is comprised of a conductive material, including but not limited to, metal, such as stainless steel. This housing 601 is conductive because it doubles as a ground return electrode. The housing 601 is shaped with a bend that is utilized to manipulate the tip into the mouth of a patient and into the dental structure, such as the tooth, that the user of the apparatus desires to irrigate.

Although a continuous housing 601, the upper portion of the housing 609, and the lower portion of the housing 610 have differing characteristics. To protect the internal elements, in an embodiment of the present invention, the upper portion of the housing 9 is thick and rigid. The lower portion of the housing 610 is comprised of a material that is both conductive and flexible, such as a flexible stainless steel tube. The lower portion of the housing 610 is comprised of a first portion 611 and a second portion 612. The first portion 611 is solid while the second lower portion 612 is porous. The porous second lower portion 612 allows an electrical discharge to occur in the lower part of the tip 600 and permeate the tip into the liquid.

Internal to the housing 601, is a center electrode conductor 603, which conducts the charge through the tip 600. This center electrode conductor 603 is insulated using a layer of insulation 606 throughout the length of the tip 600 and the center electrode conductor 603. A porous portion of insulation 608 surrounds the lower center firing electrode 604. As discussed later in accordance with different tip configurations, clearings, also called perforations, in the insulation enable embodiments of the system to fire, i.e., match the central electrode with the ground electrode. For example, the location of one or more perforations in a tip defines where the sparks, cavitation, compression, nanoparticle evolution occurs. As recognized by one of skill in the art, utilizing tips with different placements for perforations is useful in increasing the efficacy of different treatments. In a method of manufacturing embodiments of the tips, an insulating layer is placed on the center electrode and selectively removed, thereby defining the proximity of electrical coupling between the center electrode and the ground return. Electrical coupling occurs where the insulation layer has been removed.

In an embodiment of the invention, the lower perforated return electrode 605 is a ground return electrode 116, and the insulation 606 and the perforated return electrode 605 comprise a lower electrode assembly and firing chamber. In an embodiment of the present invention, the center electrode is centrally located in the tip, evenly from all walls.

In embodiments of the present invention, the center firing electrode 604 is either a positive or a negative electrode, and the lower perforated return electrode 605 is either a negative or a positive electrode. In each embodiment, the center firing electrode 4 has a charge that opposes that of the lower perforated return electrode 605. One of skill in the art will recognize that a center electrode and a ground electrode, regardless of charge, may be adapted to create the desirable electrical events within the tip of embodiments of the present invention.

Returning to FIG. 10, the lower center firing electrode 604 is embedded in the tip 600, while the lower perforated return electrode 605 is located in the outside of the tip 600. The porous second lower portion 612 of the tip 600, the porous portion of insulation 608 surrounding the lower center firing electrode 604, and the perforated return electrode 605 allow liquid solution to make contact with the lower center firing electrode 604. The conductive liquid bridges the connection between the lower perforated return electrode 605 and the lower center firing electrode 604 so that the tip can deliver acoustic waves into the area targeted by the tip. The lower center firing electrode 604 transfers the energy into the liquid solution that causes the acoustical shock wave, while the holes in the lower perforated outside return electrode 605 allow the acoustical shock wave to penetrate into the liquid solution and enable the liquid solution, which embodies the aforementioned antimicrobial properties, to flow from the inside of the tip to the dental surface being worked upon, for instance, a root canal.

Flexible outside and inside lower electrodes 607 assist in positioning the tip 600 to deliver the acoustic waves to a targeted area. Specifically, the flexible outside and inside lower electrodes 607 allow the tip 600 to be worked into the tooth or the root canal for performing the irrigation of the root canal and laterals. Many infections within a root canal are introduced during the dental procedure. Because the use of the tip of FIG. 10, for example, offers real time bioremediation during the dental process, its use reduces the introduction of foreign species to the inside of a tooth.

In an embodiment of the present invention, the electrodes utilized include silver. Water treated with silver electrodes has the highest bactericidal activity because ions of silver have the highest toxicity to bacteria; it is an anti-pathogen. Thus, the nanoparticles created by the silver electrodes also combat the bacteria and foreign particles in the canals. Further embodiments of the present invention utilize electrodes comprised from additional materials that are biologically inert. Materials used to comprise the electrodes include but are not limited to silver, copper, stainless steel, ceramic, carbon-based material, iron, and/or other conductive materials. The suspensions utilized with an embodiment of the present invention can also contain nanoparticles, which further aid in the efficacy of embodiments of the device in combating bacteria and foreign particles. In embodiments of the present invention, sonoluminescence, as described earlier, may occur during treatment and provides light at the working surface which assists an operator in confirming the actuation of the device as well as providing UV light which is known to further remediate microbial/biologic species.

As aforementioned, the tip of an embodiment of the apparatus may be removable and may be switched out with different tips that are more suited for different applications. In embodiments where the tips are not removable, the tip design may vary to maximize efficacy across varying uses.

In the tip of the embodiment in FIG. 10 an electrical discharge is produced between a centrally located electrode and a ground return and creates a cavitating bubble and therefore, ionic species, nanoparticles, pathogen killing agents etc. The cavitating bubble further produces a force capable of moving the working fluid down the inside of the ground return tube of the top, exiting the ground return tube via machined water vents, also referred to as orifices, in various tip embodiments. In tips that include these vents, the position of the vents on the tip and the shape of the vents help define the position, magnitude and direction of the exiting working fluid.

In the present application, the terms vents, holes, orifices, openings, and apertures, are used interchangeably.

Embodiments of the tips include different numbers of vents, different vent positions, and particular vent angles, which facilitate the movement of the conductive medium, including but not limited to, the working fluid in a particular direction from the inside of the dental tip, to the outside of the dental tip, into the root canal. In some embodiments of the tips, the angle and position of the vents is defined to match the known angles of laterals within a tooth. For example, that laterals in the center of the tooth exit/enter the root canal at approximately 90 degrees to the root canal, while laterals positioned towards the bottom of the root canal exit/enter the root canal at approximately 60 degrees. Matching of these angles focuses the cavitation produced species and/or the plasma into the lateral canals at optimum angles. However, depending upon the anatomical structure targeted and the cavity into which an embodiment of the device is at least partially inserted, the angles of the openings can vary anywhere from 0-180 degrees relative to a longitudinal axis.

In some embodiments of the tips of the present invention, a small amount of epoxy resin is applied to the insulating shrink tubing upon construction. The resin keeps water from firing up the tube, effectively forcing the water to egress via the engineered orifices.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The invention claimed is:

1. A method of producing a cavitation discharge, comprising:
    obtaining a hand-held electrical discharge irrigation device, comprising:
        a start stop switch to engage the device;
        a power supply to produce a first voltage;
        a circuit coupled to the power supply configured to receive a first voltage from the power supply and to convert the first voltage to a second voltage, wherein the second voltage is higher than the first voltage; and
        an output tip comprised of flexible material such that it can be positioned within a dental canal to discharge into an irrigant in the dental canal of a tooth wherein the output tip is configured to receive the second voltage, the output tip comprising an apex, wherein the output tip is coupled to the circuit, the output tip comprising:
            a first end, a second end, and a longitudinal axis extending between them;
            an electrode located in an interior space of the output tip configured to receive an electrical charge from the circuit and to release the electric discharge; and
            a ground return comprising an inside surface of the output tip, wherein a space between the electrode and the ground return comprises a first conductive medium, the first conductive medium being in contact with the electrode and the ground return to produce the electric discharge; and
            at least one opening extending through an outside surface of the output tip;
    positioning the output tip of the device adjacent to a target, wherein the target is infected tissue within the dental canal;
    engaging the start stop switch on the device to control the electric discharge; and
    utilizing the electrical discharge to create compression waves within the first conductive medium, causing the first conductive medium to exit the output tip through the at least one opening in the output tip into the irrigant, generating shock waves and ultraviolet radiation in the irrigant and causing the irrigant to irrigate the dental canal, wherein the generating transforms the irrigant into an anti-microbial agent, wherein the anti-microbial agent based on the generating providing the irrigant with an anti-microbial effect such that the irrigant destroys bacteria and microbial cells comprising the infected tissue, wherein the destroying comprises disrupting genetic systems of the bacteria and the microbial cells, wherein the irrigant is not an anti-microbial agent before the generating; and
    utilizing the start stop switch to trigger the processor to open the circuit to stop the electric discharge, wherein the anti-microbial effect of the irrigant persists in the dental canal after the electrical discharge has stopped without impacting a structural integrity of the tooth.

2. The method of claim 1, wherein the electrical discharge creates cavitation within the first conductive medium.

3. The method of claim 2, wherein sonoluminescence occurs responsive to the cavitation, and wherein light is visible to an operator of the device during operation of the device.

4. The method of claim 1, wherein the electrode opposes the inner surface at a distance,
    wherein the electrode is cylindrical,
    wherein the inner surface is cylindrical, and
    wherein the distance is equal between the electrode and the inner surface when measured from the electrode to the inner surface around the circumference of the electrode.

5. The method of claim 1, wherein the output tip further comprises an insulating layer in contact with one of the electrode and the ground return,
    wherein the insulating layer comprises at least one perforation, and
    wherein the at least one perforation defines an area for electrical coupling between the electrode and the ground return.

6. The method of claim 2, wherein the outside surface of the output tip is cylindrical.

7. The method of claim 2, wherein the at least one opening extends through the outside surface.

8. The method of claim 2, wherein the output tip further comprises:
    an insulating layer proximate to the outside surface of the output tip; and an insulating layer positioned between the inner surface and the electrode, wherein the electrode comprises an array of individual electrodes.

9. The method of claim 1, wherein the ground return is cylindrical.

10. The method of claim 1, further comprising:
monitoring, based on obtaining data from an oscilloscope, dielectric behavior of the electrode, wherein the oscilloscope is electrically coupled to the electrical discharge irrigation device.

11. The method of claim 10, further comprising:
determining, based on the data, that the electrode is degrading.

12. The method of claim 10, further comprising:
displaying, by the processor, on a monitor communicatively coupled to the processor, a graphical representation of the dielectric behavior of the electrical discharge irrigation device comprising an oscilloscope trace.

13. The method of claim 1, wherein the first conductive medium is selected from the group consisting of: water, ethylenediaminetetraacetic acid, saline, and sodium hypochlorite.

14. The method of claim 1, wherein the circuit comprises a push switch to initiate a timing circuit.

15. The method of claim 1, the circuit further comprising:
a discharge capacitor configured to receive the second voltage; and
at least one of a transistor or a controlled rectifier coupled to the discharge capacitor configured to receive the second voltage and to provide the second voltage to the output tip, wherein the output tip is coupled to the at least one of the transistor or the controlled rectifier.

16. The method of claim 1, wherein the irrigant and the first conductive medium comprise water.

17. The method of claim 1, wherein the irrigant destroys the bacteria and the microbial cells without damaging healthy tissue proximate to the infected tissue.

* * * * *